United States Patent
Kurz et al.

(10) Patent No.: US 6,770,678 B1
(45) Date of Patent: Aug. 3, 2004

(54) LYOPHILISATES HAVING IMPROVED RECONSTITUTABILITY

(75) Inventors: Thelka Kurz, Darmstadt (DE); Ludwig Krueger, Aschafferburg (DE); Brigitte Hesse, Fränkisch-Crumbach (DE); Arnd Karnatz, Rossdorf (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/889,930

(22) PCT Filed: Jan. 26, 2000

(86) PCT No.: PCT/EP00/00569
§ 371 (c)(1),
(2), (4) Date: Oct. 3, 2001

(87) PCT Pub. No.: WO00/44354
PCT Pub. Date: Aug. 3, 2000

(30) Foreign Application Priority Data

Jan. 28, 1999 (DE) .......................................... 199 03 275

(51) Int. Cl.⁷ ...................... A61K 31/155; A61K 31/40; A61K 31/135
(52) U.S. Cl. ........................ 514/634; 514/408; 514/646
(58) Field of Search ................................. 514/408, 634, 514/646

(56) References Cited

U.S. PATENT DOCUMENTS

| | | | |
|---|---|---|---|
| 4,002,748 A | | 1/1977 | Bornstein et al. |
| 5,066,647 A | * | 11/1991 | Palepu et al. ................ 514/110 |
| 5,591,754 A | * | 1/1997 | Lang et al. .................. 514/331 |
| 5,679,645 A | | 10/1997 | Yoshihiro |
| 5,744,641 A | * | 4/1998 | Gericke et al. ............. 564/228 |
| 5,753,680 A | * | 5/1998 | Gericke et al. ............. 514/331 |

OTHER PUBLICATIONS

Franks F:"Freeze drying of Bioproducts . . . " European Journal of Pharmaceutics and Biopharmaceutics, NL, Elsevier Science Publishers, Amsterdam, vol. 45, No. 3, May 1, 1998 (May 1, 1998). pp. 221–229.

* cited by examiner

*Primary Examiner*—Shengjun Wang
(74) *Attorney, Agent, or Firm*—Millen, White, Zelano & Branigan, P.C.

(57) ABSTRACT

The present invention relates to lyophilisates having an improved dissolution rate which can be reconstituted in a particle-free manner, which is achieved by re-warming the solutions already drawn off to from 30° to 95° C. directly in the freeze drier.

18 Claims, No Drawings

LYOPHILISATES HAVING IMPROVED RECONSTITUTABILITY

The present invention relates to lyophilisates having an improved dissolution rate and reconstitutability, and to a process for their preparation.

Lyophilisation, also known as freeze drying, is a long-known and widely used method for the preservation of certain substances under gentle conditions, such as, for example, heat-sensitive foods or especially medicaments. In this method, the substances are dried in the frozen state and can be restored into the original state particularly easily on addition of water or another solvent. In this method, the first step is generally freezing of the starting materials at temperatures down to −70° C. The water is subsequently removed from them by sublimation during the drying process, which is carried out in pressure-tight containers (lyophilisators) under a high vacuum, giving the freeze-dried substance.

Lyophilisation is employed in particular for the preservation of sensitive medicaments, since it is very important in the case of medicaments in particular that they do not change during storage, i.e. their structure does not change, rearrange or even decompose, which would mean a considerable impairment with respect to their efficacy.

Efforts are always made during freeze drying to incorporate the largest possible amount of active ingredient into the smallest possible volume. This results in concentrations in the vicinity of the saturation concentration of the active ingredient often being employed. This is necessary for the economic efficiency of the processes.

In theses cases, however, the lyophilisate often cannot be reconstituted in a particle-free manner after freeze drying has been carried out, meaning that parenteral administration is no longer possible. This is attributed to crystals which have formed due to cooling after the saturation solubility has been exceeded. The dissolution rate of crystals is significantly slower than that of molecules in amorphous form.

The object of the present invention was therefore to provide a process for the preparation of lyophilisates which have an improved dissolution rate and can be reconstituted in a particle-free manner, even if they are metered close to the saturation concentration.

Surprisingly, it has been found that warming of the solution already prepared for the freeze-drying process directly in the freeze drier and rapid cooling from this elevated temperature to the freezing temperature gives lyophilisates which achieve the desired advantageous properties.

The invention therefore relates to a process for the preparation of lyophilisates having an improved dissolution rate, characterised in that the corresponding solutions already drawn off for lyophilisation, which have, if necessary, previously been warmed in order to accelerate dissolution of the substance, filtered—optionally sterile-filtered—and drawn off, are re-warmed to from 30° to 95° C. directly in the vials in the freeze drier, and the freezing phase is then carried out rapidly from this elevated temperature to the desired low freeze-drying temperature.

The feature "rapidly" in this connection means a period of from 10 minutes to 4 hours, preferably from 30 minutes to 2 hours, very particularly preferably from 30 minutes to 1 hour.

The desired freeze-drying temperature can be down to −70° C., a temperature of about −50° C. preferably being used.

In the conventional freeze-drying process, the substance or active ingredient is warmed in order to accelerate dissolution. The dissolution is followed, in the case of sterile preparation, which is usual in the case of medicaments, by the steps of sterile filtration and drawing-off. These two steps may, depending on the size of the batch, take a few hours. In the process, the solutions automatically cool to room temperature. The freeze drier is thus then charged at room temperature, and the freezing phase is then carried out as quickly as possible from room temperature to about −50° C. The drying phase in the freeze drier then commences.

In the process according to the invention, the dissolution, filtration or sterile filtration and the drawing-off are carried out analogously to the known process. Then, however, the freeze drier is charged with the corresponding prepared vials at room temperature, and these vials are re-warmed to 30°–95° C. in the apparatus. The freezing phase is started from this elevated temperature and brought to the desired freezing temperature as quickly as possible. The drying phase is then carried out in the usual manner.

Due to the re-warming of the solutions, the saturation solubility is significantly increased, which is attributable to the reduction in the size of the water clusters. The increased solubility thus results in improved hydration. In the case of rapid cooling, firstly the water molecules lack the time to form relatively large clusters, and secondly the active ingredient molecules lack the time to arrange themselves into crystal nuclei. The resultant product is accordingly amorphous and can be reconstituted in a particle-free manner.

The warming of the solutions takes place to temperatures of from 30° to 95° C., temperatures in the range from 30° to 70° C. preferably being selected.

The process according to the invention thus enables significantly higher concentrations to be introduced into a volume. The drying time is thus reduced and the economic efficiency of the process is increased.

The lyophilisates prepared in this way exhibit an improved dissolution rate and can be reconstituted in a particle-free manner although they can be metered close to the saturation concentration.

The invention also relates to the preparation of lyophilisates of the substance 2-methyl-5-methylsulfonyl-4-(1-pyrrolyl)benzoylguanidine methanesulfonate by the process described here (see Example 1). This substance (EMD 96785), which is known, for example, from DE 4430861, is an NHE inhibitor which blocks the $Na^+/H^+$ ion pump in the myocardial cells. This prevents overacidification of the cells in the case of an infarction, which results in the death of myocardial tissue.

The invention also relates to the preparation of lyophilisates of the substance N-[2-methyl-4,5-bis(methylsulfonyl)benzoylguanidine hydrochloride by the process described here (see Example 2).

This substance (EMD 87580), which is known, for example, from EP 0 758 644 A1, is likewise an NHE inhibitor which blocks the $Na^+/H^+$ ion pump in the myocardial cells. This prevents overacidification of the cells during an infarction, which results in death of myocardial tissue.

The invention also relates to the preparation of lyophilisates of the substance 4-isopropyl-3-methylsulfonylbenzoylguanidine methanesulfonate by the process described here.

This substance (cariporide), which is known, for example, from EP 589 336, in likewise an NHE inhibitor.

The invention furthermore relates to pharmaceutical preparations comprising at least one lyophilisate according to the invention.

The pharmaceutical preparations can be used as medicaments in human or veterinary medicine. Suitable excipients are organic or inorganic substances which are suitable for enteral (for example oral), parenteral or topical administration and do not react with the lyophilisates, for example water, vegetable oils, benzyl alcohols, alkylene glycols, polyethylene glycols, glycerol triacetate, gelatin, carbohydrates, such as lactose or starch, magnesium stearate, talc or Vaseline. Suitable for oral administration are, in particular, tablets, pills, coated tablets, capsules, powders, granules, syrups, juices or drops, suitable for rectal administration are suppositories, suitable for parenteral administration are solutions, preferably oil-based or aqueous solutions, furthermore suspensions, emulsions or implants, and suitable for topical application are ointments, creams or powders. The preparations indicated may have been sterilised and/or comprise assistants, such as lubricants, preservatives, stabilisers and/or wetting agents, emulsifiers, salts for modifying the osmotic pressure, buffer substances, colorants, flavours and/or a plurality of further active ingredients, for example one or more vitamins.

The preparations preferably comprise the lyophilisates, for example, for the preparation of injection preparations.

Even without further details, it is assumed that a person skilled in the art can utilise the above description in the broadest scope. The preferred embodiments are therefore merely to be regarded as descriptive disclosure, but in no way as a disclosure which is limiting in any way.

The complete disclosure content of all applications and publications mentioned above and below are incorporated into this application by way of reference.

EXAMPLE 1 a)

100 mg of 2-methyl-5-methylsulfonyl-4-(1-pyrrolyl) benzoylguanidine methanesulfonate (an NHE inhibitor) are dissolved in 20 ml of water by warming to 40° C. in order to accelerate the dissolution. The solution is subsequently sterile-filtered and drawn off into vials suitable for freeze drying. In the process, the solution cools to room temperature. The freeze drier is charged with the vials at room temperature, and these vials are subsequently re-warmed to about 50° C. The freezing is then carried out from +50° C. to −50° C. within 1 hour. The drying phase then proceeds in the conventional manner.

The resultant lyophilisates are amorphous and can be reconstituted in a particle-free manner.

b) Comparative Example 100 mg of 2-methyl-5-methylsulfonyl-4-(1-pyrrolyl) benzoylguanidine methanesulfonate are again dissolved in 20 ml of water with warming to 40° C. The solution is sterile-filtered and drawn off, during which the solution cools to room temperature.

The vials are then cooled from room temperature to −50° C. over the course of 1 hour in the freeze drier and frozen.

In this conventional process, crystal formation occurs even during the lyophilisation, which results in the lyophilisates not dissolving completely during reconstitution. In order to obtain a lyophilisate comparable to a), the concentration here had to be reduced to 50 mg/20 ml.

However, this means that a higher concentration of the active ingredient can be selected in the process according to the invention and nevertheless lyophilisates having an improved dissolution rate are obtained.

EXAMPLE 2

100 mg of N-[2-methyl-4,5-bis(methylsulfonyl)] benzoylguanidine hydrochloride are dissolved in 10 ml of water by warming to 40° C. The solution is subsequently sterile-filtered and drawn off into vials or ampoules suitable for freeze drying. The solution cools to room temperature in the process.

The freeze drier is cooled down to −59° C. The vials filled with the solution are warmed to +40° C. in a drying cabinet and subsequently introduced into the freeze drier, which has already been cooled down to −50° C. The solution is frozen as quickly as possible. The drying phase is then carried out in the conventional manner. warming of the vials in the freeze drier followed by cooling (as described in example 1) is likewise possible.

What is claimed is:

1. A process for preparing a lyophilisate, having an improved dissolution rate, of 2-methyl-5-methylsulfonyl-4-(1-pyrrolyl)benzoylguanidine methanesulfonate, N-[2-methyl-4,5-bis-(methylsulfonyl)benzoyl]guanidine hydrochloride or 4-isopropyl-3-methylsulfonylbenzoylguanidine methanesulfonate, comprising dissolving 2-methyl-5-methylsulfonyl-4-(1-pyrrolyl)benzoylguanidine methanesulfonate, N-[2-methyl-4,5-bis(methylsulfonyl)benzoyl]guanidine hydrochloride or 4-isopropyl-3-methylsulfonylbenzoylguanidine methanesulfonate to form a solution suitable for lyophilization by optionally warming the solution to accelerate dissolution, filtering the solution, placing the solution into a freeze drier in a vial, and then warming the solution to 30° C. to 95° C. followed by rapidly producing the freeze phrase from the elevated temperature.

2. A process according to claim 1, wherein the solution is warmed to 30° C. to 60° C.

3. A process according to claim 2, wherein the solution comprises 2-methyl-5-methylsulfonyl-4-(1-pyrrolyl) benzoylguanidine methanesulfonate.

4. A process according to claim 2, wherein the solution comprises N-[2-methyl-4,5-bis-(methylsulfonyl)benzoyl] guanidine hydrochloride.

5. A process according to claim 2, wherein the solution comprises 4-isopropyl-3-methylsulfonylbenzoylguanidine methanesulfonate.

6. A process according to claim 2, wherein lowering the temperature to the freezing temperature takes place over from 10 minutes to 4 hours.

7. A process according to claim 2, wherein lowering the temperature to the freezing temperature takes place over from 30 minutes to 2 hours.

8. A process according to claim 2, wherein lowering the temperature to the freezing temperature takes place over from 30 minutes to 1 hour.

9. A process according to claim 2, wherein the freezing temperature is down to −70° C.

10. A process according to claim 2, wherein the freezing temperature is about −50° C.

11. A process according to claim 2 further comprising drying the solution after the lowering of the temperature.

12. A process according to claim 2, wherein the filtering is sterile filtering.

13. A process according to claim 2, wherein the temperature of the solution is at room temperature when placed into the freeze dryer.

14. A lyophilisate of 2-methyl-5-methylsulfonyl-4-(1-pyrrolyl)benzoylguanidine methanesulfonate, N-[2-methyl-4,5-bis-(methylsulfonyl)benzoyl]guanidine hydrochloride or 4-isopropyl-3-methylsulfonylbenzoylguanidine methanesulfonate, that has been prepared by the process according to claim 1.

15. A pharmaceutical composition comprising a lyophilisate of claim 14.

16. A lyophilisate of N-[2-methyl-4,5-bis-(methylsulfonyl)benzoyl]guanidine hydrochloride, that has been prepared by the process according to claim 1.

17. A lyophilisate of 2-methyl-5-methylsulfonyl-4-(1-pyrrolyl)benzoylguanidine methanesulfonate, that has been prepared by the process according to claim 1.

18. A lyophilisate of 4-isopropyl-3-methylsulfonylbenzoylguanidine methanesulfonate, that has been prepared by the process according to claim 1.

* * * * *